(12) United States Patent
Choi

(10) Patent No.: US 9,446,128 B2
(45) Date of Patent: Sep. 20, 2016

(54) COMPOSITION COMPRISING EGG WHITE COMBINED CHALCANTHITE FOR PREVENTING OR TREATING CANCER

(75) Inventor: Eun A Choi, Gyeongsangnam-do (KR)

(73) Assignee: Eun A. Choi, Gyeongsangnam-Do (KR)

( * ) Notice: Subject to any disclaimer, the term of this patent is extended or adjusted under 35 U.S.C. 154(b) by 1962 days.

(21) Appl. No.: 12/398,865

(22) Filed: Mar. 5, 2009

(65) Prior Publication Data

US 2010/0166882 A1    Jul. 1, 2010

(30) Foreign Application Priority Data

Dec. 30, 2008  (KR) ........................ 10-2008-0136873

(51) Int. Cl.
| | | |
|---|---|---|
| A61K 33/34 | (2006.01) | |
| A61K 45/06 | (2006.01) | |
| A23L 1/304 | (2006.01) | |

(52) U.S. Cl.
CPC ................ *A61K 45/06* (2013.01); *A23L 1/304* (2013.01); *A61K 33/34* (2013.01); *A23V 2002/00* (2013.01)

(58) Field of Classification Search
None
See application file for complete search history.

(56) References Cited

FOREIGN PATENT DOCUMENTS

| | | |
|---|---|---|
| EP | 1614414 A2 | 1/2006 |
| JP | H01095744 A | 4/1989 |
| JP | 2005-350420 A | 12/2005 |
| JP | 2008-505922 A | 2/2008 |
| JP | 2008-543885 A | 12/2008 |
| KR | 10-2000-0017719 A | 4/2000 |
| KR | 2003-0021857 A | 3/2003 |
| KR | 10-2003-0063914 A | 7/2003 |
| RU | 2473353 C1 | 1/2013 |
| WO | WO-2006-017179 A1 | 2/2006 |
| WO | WO-2006-135965 A1 | 12/2006 |
| WO | WO-2008-028497 A1 | 3/2008 |

OTHER PUBLICATIONS

Luck et al., The Role of Copper in Protein Foams, Feb. 2008, Food Biophysics, 3: 255-260.*
AOMicroWater Jun. 2008, http://web.archive.org/web/20080621002228/http://www.aomicrowater.com/english/en_bamboo_salt.htm.*
CRichardson, 2005, Wiley-VCH, Copper Compounds, pp. 1-30.*
Sorenson, J.R.J. et al., "Co-treatment with copper compounds dramatically decreases toxicities observed with cisplatin cancer therapy and the anticancer efficacy of some copper chelates supports the conclusion that copper chelate therapy may be markedly more effective and less toxic than cisplatin therapy", Current Medicinal Chemistry, 2007, 1499-1503, 14.
Hwang, K. et al., "Increased antimutagenic and anticlastogenic effects of *Doenjang* (Korean fermented soybean paste) prepared with bamboo salt", Journal of medicinal Food, 2008, 717-722, 11.
European Search Report dated Feb. 6, 2013 in European Application No. 09836258.5.
Office Action dated May 28, 2013 in Japanese Application No. 2011-544351.
Office Action dated May 30, 2014 in Vietnamese Application No. 1-2011-01766.
Yang, J.S. et al., "Pharmacological evaluation of bamboo salt", Journal of Applied Pharmacology, 1999, 178-184, 7.
Office Action dated Aug. 16, 2013 in Filipino Application No. 1-2011-501327.
Office Action dated Apr. 27, 2012 in Australian Application No. 2009334202.
Office Action dated Sep. 29, 2012 in Chinese Application No. 200980153534.5.

* cited by examiner

*Primary Examiner* — Terry A McKelvey
*Assistant Examiner* — Catheryne Chen
(74) *Attorney, Agent, or Firm* — Saliwanchik, Lloyd & Eisenschenk

(57) ABSTRACT

The present invention relates to a composition comprising an egg white combined chalcanthite component for preventing or treating cancer, and more particularly, to a composition for preventing or treating cancer, which comprises egg white combined chalcanthite prepared by mixing a roasted chalcanthite with egg white to reduce the toxicity of the chalcanthite or comprises a mixture of the egg white combined chalcanthite and a bamboo salt, and a method for preparing the same. The composition comprising the egg white combined chalcanthite exhibits excellent anti-cancer activity, and thus is usefully applicable to pharmaceutical preparations for preventing or treating cancer or the manufacture of health functional foods.

17 Claims, 8 Drawing Sheets

HepG2

NCI-H460

SW480

MCF-7

COMPOSITION COMPRISING EGG WHITE COMBINED CHALCANTHITE FOR PREVENTING OR TREATING CANCER

CROSS-REFERENCE TO RELATED APPLICATION

The application claims the benefit under 35 U.S.C. §119 of Korean Patent Application No. 10-2008-0136873, filed Dec. 30, 2008, which is hereby incorporated by reference in its entirety.

FIELD OF THE INVENTION

The present invention relates to a composition comprising an egg white combined chalcanthite for preventing or treating cancer, and more particularly, to a composition for preventing or treating cancer, which comprises only an egg white combined chalcanthite prepared by mixing a chalcanthite with an egg white to remove the toxicity of the chalcanthite or comprises a mixture of the egg white combined chalcanthite and a bamboo salt, and a method for preparing the same.

BACKGROUND OF THE INVENTION

Cancer refers to a class of diseases which start with uncontrollable cell proliferation, then invade and destroy adjacent normal tissues and organs, can further create new growing sites for cancer cells, and finally carry off individuals. Over the past 10 years, to conquer cancer, there have been remarkable developments in modulating cell cycle and apoptosis and seeking new targets including oncogenes or tumor suppressor genes. Nevertheless, cancer incidence continues to increase as the civilization advances.

At present, a cancer therapy depends on surgical operation, radiotherapy, and chemotherapy of administering forty kinds of anti-cancer materials exhibiting potent cytotoxicity. However, most of these therapies are limited to only patients in early stage and special cancers, and thus cancer mortality is being increased continuously.

Furthermore, since most of anticancer drugs are highly toxic chemicals, anti-cancer drugs with low toxicity, particularly natural product-derived anti-cancer drugs, are being developed continually.

A chalcanthite, which is a kind of sulfate minerals composed of copper sulfate, contains $CuSO_4 \cdot 5H_2O$ mainly. The chalcanthite is a natural mineral with a very small amount of other minerals mixed, and is a blue crystal. The chalcanthite belongs to a triclinic system, is glassy-lustrous, and shows semi-transparent blue color. It is known that the chalcanthite is used for emetics, insecticides, pigments, fixatives, electrolytes, etc. There is a fear of toxicity because chalcanthite is a crude drug from mineral sources. For this reason, there has been a limitation in making use of the chalcanthite for clinical use actually, and further the fact that chalcanthite can be used for anti-cancer drugs has never been known to the public.

A Bamboo salt was first invented by Il-hoon Kim (pen name is In-san). The bamboo salt is prepared by synthesizing a bamboo and a salt using a roasting process. Herein, the bamboo acts as cytoneogenesis to generate new cells, and the salt acts as sterilization and antisepsis. Specifically, the salt filled into the bamboo is roasted several times in a furnace at a high temperature, thus removing toxic materials from the salt and enhancing pharmaceutical effect. The bamboo salt has several advantageous effects such as the pharmacological effect of treating causes of inflammatory diseases by strengthening a stomach which is considered as a basis of a human body, the blood clarification effect for clarifying blood, the effect of detoxification and elimination of body waste accumulated in a body, and the effect for converting physical constitution type from an acidic type to a weak alkaline type. In addition, it is known that the bamboo salt has three to four times stronger anti-inflammatory action and sterilization ability against bacteria than the general salt, and thus such sterilization action leads to alleviation of fever in a human body.

The inventors found out that the egg white combined chalcanthite, in which the toxicity of chalcanthite was neutralized with the egg white, induced apoptosis of cancer cells to suppress the growth of the cancer cells, and thus were applicable to a natural anti-cancer drug. Furthermore, the inventors found out that the egg white combined chalcanthite was solely used or a composition comprising a mixture of the egg white combined chalcanthite and the bamboo salt can be used as an anti-cancer drug, thereby completing the present invention.

BRIEF SUMMARY

Embodiments of the present invention are directed to a composition for preventing or treating cancer, which comprises egg white combined chalcanthite as an effective component.

Embodiments of the present invention are also directed to a health functional food for preventing or ameliorating cancer, which comprises egg white combined chalcanthite as an effective component.

Embodiments of the present invention are also directed to methods for preparing egg white combined chalcanthite, an embodiment comprising: (a) heating and dehydrating a chalcanthite, until the entire chalcanthite turns grey; (b) cooling the dehydrated chalcanthite, and pulverizing the chalcanthite; and (c) mixing the chalcanthite with egg white.

DETAILED DESCRIPTION

In one aspect, the present invention provides a composition for preventing or treating cancer, which comprises egg white combined chalcanthite as an effective component.

In the present invention, the term "egg white combined chalcanthite" means a mixture of egg white and a chalcanthite, and in an embodiment may be prepared by roasting the chalcanthite (natural mineral mainly composed of $CuSO_4 \cdot 5H_2O$) to dehydrate it, pulverizing the dehydrated chalcanthite, and then mixing the pulverized chalcanthite react with the egg white to trigger the reaction therebetween. In the egg white combined chalcanthite so prepared, the toxicity of the chalcanthite is neutralized by the egg white, so that the toxicity is reduced or removed and pharmaceutical properties are increased.

The composition of the present invention may further comprise a bamboo salt.

The bamboo salt used in the present invention may be goods on the market or may be prepared personally. Here, the bamboo salt may be one that is prepared through an orthodox nine-times-melting bamboo salt fabrication method that is disclosed in books, entitled 'Universe and Miraculous Drug (1980)' and 'Miraculous Drug (1986)' of Il-hoon Kim (pen name is In-san) who is known as a bamboo salt inventor, but the bamboo salt of the present invention is not limited thereto. For example, this bamboo salt fabrication method comprises: putting a bay salt produced from the west coast in the Republic of Korea into a timber bamboo and closing the timber bamboo with an ocher stopper; laying the timber bamboos filled with the bay salt in an iron can compactly; roasting the timber bamboos using a pine tree as a firewood to thereby burn out the timber bamboos; milling a remaining salt pillar and then putting the milled salt into a new timber bamboo again; repeating the above-described processes eight times; and, in a ninth processing time, melting down the salt by increasing heating power through the addition of pine resin.

The egg white combined chalcanthite and the bamboo salt contained in the composition of the present invention may be powdered. Also, when the composition of the present invention comprises both the egg white combined chalcanthite and the bamboo salt, the powdered egg white combined chalcanthite and the bamboo salt may be mixed at various ratios ranging from 1:99 to 99:1 by weight, desirably 1:5 to 1:50 by weight, most desirably 1:5, 1:10, 1:15, 1:25, and 1:30.

When the composition of the present invention is used for oral preparations, the amount of the bamboo salt powder may be equal to or larger than that of the egg white combined chalcanthite powder. If a person is young, weak, old, or sick, the amount of the bamboo salt should be increased. However, if a person has a strong body, the amount of the egg white combined chalcanthite may be gradually increased, and can be administered as a medicine up to a ratio of the egg white combined chalcanthite to the bamboo salt ranging from 1:10 to 1:5.

Furthermore, in the case where the composition is used for coating preparations that are applied to the skin of the body and used for cleaning and spraying, or used for enema, the amount of the egg white combined chalcanthite may be increased, and the egg white combined chalcanthite may also be used singly.

The egg white combined chalcanthite composition of the present invention may have cancer-suppressing ability through improvement of activity of caspase-3.

In specific embodiments of the present invention, in the case of treating liver cancer cells (HepG2), colon cancer cells (SW480), breast cancer cells (MCF-7), lung cancer cells (NCI-H460) with the egg white combined chalcanthite, it can be observed that the suppression of cell proliferation is concentration-dependent. Furthermore, in the case of treating liver cancer cells and lung cancer cells with the egg white combined chalcanthite, it can be observed that nuclear fragmentation and chromatin condensation occur because apoptosis is induced. In addition, the cancer-suppressing ability of the egg white combined chalcanthite composition is observed at a protein level, and resultantly it can be confirmed that the activation of caspase-3 protein induces apoptosis so that the composition containing the egg white combined chalcanthite suppresses the growth of cancer cells.

The egg white combined chalcanthite composition of the present invention may be used for preventing or treating cancer. In the present disclosure, the term "preventing" means every practice that suppresses the development of diseases and suspends the onset of diseases by administering the composition, and the term "treating" means every practice that improves the diseases or changes the conditions favorably by administering the composition.

The composition of the present invention may be applicable to most of cancers, for example, liver cancer, breast cancer, lung cancer, colon cancer, stomach cancer, pancreatic cancer, uterine cancer, prostate cancer, bone cancer, glioma, leukemia, etc. Desirably, the composition of the present invention may be applied to cancers of liver, colon, breast and lung, but is not limited thereto.

The composition comprising the egg white combined chalcanthite of the present invention as an effective component may be used as a pharmaceutical composition by further comprising pharmaceutically acceptable carriers. In this case, the composition can be prepared together with the carriers. Also, the composition of the present invention may be used as a single-agent or may be used as a complex agent with other effective components improving drug efficacy.

In the present invention, the term "pharmaceutically acceptable carriers" refers carriers or diluents that do not inhibit biological activities and characteristics of administered chemicals without stimulating living organisms. The pharmaceutically acceptable carrier in a composition prepared in liquid solution may comprise carriers available for a living body, for example, saline, sterilized water, linger, buffered saline, albumin injection, dextrose solution, malto dextrine solution, glycerol, ethanol, and a mixture containing at least one of them. If necessary, typical additives such as antioxidant, buffering agent and bacteriostatic agent may be added to the carrier. Also, it is possible to prepare formulations for injection use (e.g., aqueous solution, suspension, emulsion, or the like), pills, capsules, granules, or tablets, by further adding diluents, dispersing agents, surfactants, binding agents, and lubricants.

The composition of the present invention may be applicable to any formulation containing it as an effective component, and formed in oral or parenteral formulation. The pharmaceutical formulation of the present invention may include shapes suitable for oral, rectal, nasal, topical, subcutaneous, vaginal or parenteral administration, for inhalation, or for insufflation. Herein, the parenteral administration may include intramuscular, subcutaneous and intravenous administration.

The formation for oral administration including the composition of the present invention may be prepared in the form of, for example, tablet, troche, lozenge, water-soluble or lipophilic suspension, formulated powders or granule, emulsion, hard or soft capsule, syrup, elixir, or the like. To prepare the composition in the form of tablets and capsules, the composition may include binders (e.g., lactose, saccharose, sorbitol, manitol, starch, amylopectin, cellulose, or gelatin), excipients (e.g, dicalcium phosphate), disintegrants (e.g., corn starch, or sweet potato starch), and lubricants (e.g., magnesium stearate, calcium stearate, sodium stearyl fumarate, or polyethylene glycol wax). In the case of capsule formations, liquid carriers such as fatty oil may be further added besides the above-described substances.

The formation for parenteral administration comprising the composition of the present invention may be prepared in the form of injection type such as subcutaneous injection, intravenous injection and muscular injection, in the form of suppository injection type, or in the form of spray type such as aerosols that can be inhaled through a respiratory tract. To prepare the formations for injection use, the composition of the present invention is mixed with stabilizer or buffering agent in water to thereby fabricate solution or suspension, and the fabricated solution or suspension can be prepared for unit dose of ampules or vials. For suppository injection, the formation may be prepared in the form of compositions for rectal administration such as enema or suppository including typical suppository base, e.g., cocoa butter or other glycerides. In the case of preparing the spray-type formations such as aerosols, propellants may be mixed with additives such that water-dispersed condensed material or moisturized powder is dispersed.

In another aspect, the present invention provides a method of preventing or treating cancer using a composition comprising an egg white combined chalcanthite.

In the present invention, the treating of diseases may comprise administering a pharmaceutical composition comprising an egg white combined chalcanthite. In the present invention, the term "administering" means introducing the pharmaceutical composition of the present invention to patients through appropriate methods.

The composition of the present invention can be administered through a variety of administration routes, for example, an oral administration route or a parenteral administration route only if the composition can reach a target organ. To be specific, the composition may be administered through general methods, for example, oral, rectal, topical, intravenous, intrapenitoneal, intramuscular, intraarterial, transdermal, intranasal, inhalation, or intraocular administration, or intradermal route. Desirably, the composition may be administered through oral or cutaneous administration.

The treating method of the present invention comprises administering the composition of the present invention with pharmaceutically acceptable dose. It is obvious to a person with ordinary skill in the art that total one-day dosage may be determined by a doctor within the scope of proper medical judgment. The therapeutically effective dose for a specific patient may be differently determined according to various factors or pseudo-factors well-known in the medical field, for example, the kind and extent of reaction to be achieved, whether or not other formulations are used depending on circumstances, specific compositions, age of the patient, body weight, general heath conditions, gender, diet, administration route, and distribution ratio of composition, treatment duration, drugs used together or simultaneously with the specific compositions, and so forth. Therefore, the one-day effective dose of the pharmaceutical composition suitable for the objective of the present invention may be determined in consideration of the aforesaid. Most desirably, the one-day effective dose of the pharmaceutical composition may be administered in a range of 0.1 g to 30 g based on the weight of the egg white combined chalcanthite powder. However, there is no limitation in effective dose when the composition is used as external preparations such as enema, cutaneous use, and the like.

Furthermore, the treating method of the present invention can be applied to any animal in which cancer may be developed. Herein, the animal may include not only humans and primates, but also livestock such as cows, pigs, sheep, horses, dogs, and cats.

Particularly, in oral administration of the composition of the present invention, it is possible to swallow the composition with water, with water in which ginger and licorice root are mixed and decocted, with water containing the extract of the root bark of *ulmus devidiana* var, or with saliva. As an intake method, there is a method of taking the capsule containing the composition through the above-described methods as well as a method of directly taking the composition. In this case, a method of taking the capsule containing the composition with saliva is better than a method of taking the capsule with water or beverage. The composition may be administered such that it is mixed into food and beverage in a small amount. For example, the mixture may be added into rice paste or roasted garlic, or the egg white combined chalcanthite powder may also be added to bamboo salt soybean.

In specific embodiments of the present invention, the egg white combined chalcanthite of the present invention was administered to cancer patients together with the bamboo salt, and anti-cancer effect was then observed. Resultantly, it can be observed that the administration of the egg white combined chalcanthite with the bamboo salt is effective for treating breast cancer, leukemia, stomach cancer, colon cancer, lung cancer, bone cancer, dysplasia of cervix uteri, thyroid cancer, etc.

In another aspect, the present invention provides a health functional food for preventing or ameliorating cancer, which comprises an egg white combined chalcanthite as an effective component.

The health functional food of the present invention may further comprise bamboo salt besides the egg white combined chalcanthite.

The composition of the present invention may be prepared by further containing food additives, which are sitologically acceptable, and may be available for a health functional food for preventing or ameliorating cancer. The health functional food of the present invention may include formations such as tablets, capsules, pills and liquid.

Foods into which the composition of the present invention can be added may include, for example, various kinds of groceries, beverage, gum, tea, vitamin complex, health functional food.

The term "health functional food" defined in the present disclosure means foods manufactured and processed by using raw materials and components having useful functions to a human body. The term "functional" means that intake of food is directed to controlling nutriments on the structure and function of a human body or achieving the useful effect for preservation of health such as physiological action.

The composition of the present invention may be added to foods and beverages for the purpose of preventing or ameliorating cancer. Here, the amount of the composition added into the food or beverage may be in a range of 0.01 wt % to 10 wt % of the total food weight. For example, when the total volume of the health beverage is 100 ml, the composition may be added in an amount of 0.01 g to 5 g, desirably 0.5 g to 1 g.

In another aspect, the present invention provides a method for preparing egg white combined chalcanthite, the method comprising: (a) heating and dehydrating a chalcanthite, until the entire chalcanthite turns grey; (b) cooling the dehydrated chalcanthite, and pulverizing the chalcanthite; and (c) mixing the chalcanthite with egg white.

Herebelow, one method for preparing the egg white combined chalcanthite according to the present invention will be described as a series of steps:

In the step (a), a chalcanthite (natural mineral containing $CuSO_4 \cdot 5H_2O$) is heated and then dehydrated. The heating of the chalcanthite may be performed using a typical method that is well-known in the art. Preferably, the chalcanthite is put into a caldron, and then roasted with gas fire, wood fire or charcoal fire. During heating, the chalcanthite may be turned upside down to uniformly receive heat while carefully watching a change in color at every 3 to 5 hours. Although the appropriate heating duration may vary with one-time use amount, it may be in the range of 10 to 24 hours. The chalcanthite may be heated until whole the chalcanthite turn grey to be in a state of dehydrated chalcanthite.

In the step (b), the chalcanthite heated and dehydrated in the step (a) is cooled, and then pulverized. The dehydrated chalcanthite should be cooled until heat is completely released. Here, the moisture content of the chalcanthite may range from 0% to 5%. After the dehydrated chalcanthite is completely cooled, the chalcanthite is pulverized finely. Thereafter, the pulverized chalcanthite may be put into a plastic bag or an airtight container so as to prevent moisture from being absorbed thereinto, and then kept in a dry place.

In the step (c), the chalcanthite powder prepared in the step (b) is mixed with egg white to trigger the reaction between the chalcanthite and the egg white, which reduces or removes the toxicity of the chalcanthite and increases pharmaceutical properties. Herein, an egg should be separated into an egg yolk and an egg white, and then only the egg white is used in the present invention. The egg may be a homegrown egg, preferably Korean ogol chicken egg. The dehydrated chalcanthite powder prepared in the step (b) is mixed with the egg white. At this time, the mixing ratio may be set such that 600 g of the chalcanthite powder may be mixed with 140 to 400 g of egg white that is obtained from 7 to 20 eggs. While watching a mixed state, the amount of egg white may be adjusted and the chalcanthite and the egg white may uniformly be mixed using a tool, e.g., wood spatula, which rarely participates in the reaction. In addition, the mixing may be performed in a vessel that is inactive in chemical reaction, for example, an earthen vessel, a ceramic ware, or an elvan vessel. During the mixing, special attention should be paid because much heat is generated due to reaction heat.

Furthermore, if the amount of egg white is too small during the mixing, it is difficult to neutralize the toxicity of the dehydrated chalcanthite powder. On the contrary, if the amount of egg white is too great, the reaction heat is very weak or not generated, making it difficult to achieve the mixing effect sufficiently. Thus, the amount of egg white should be adjusted carefully. After the chalcanthite and the egg white are sufficiently mixed, the mixture may be cooled until the reaction heat is completely released.

Moreover, in an embodiment, the method for preparing the chalcanthite according to the present invention may further comprise, after the step (c), (d) cooling the mixture of the step (c), and then pulverizing the cooled mixture after the step (c).

In the step (d), the mixture prepared in the step (c) is cooled until the heat is completely released, and the chalcanthite with the egg white mixed is pulverized finely to form egg white combined chalcanthite powders. Consequently, by pulverizing the egg white combined chalcanthite, the egg white combined chalcanthite can be effectively used for pharmaceutical or sitological preparations, and further its reaction area is increased, thus maximizing therapeutic activity.

In the egg white combined chalcanthite prepared through the methods taught herein, the detrimental characteristics of the chalcanthite can be reduced but pharmaceutical properties are enhanced, and therefore it is applicable to a pharmaceutical or sitological composition for preventing or treating cancer.

EXAMPLES

Figure 1:
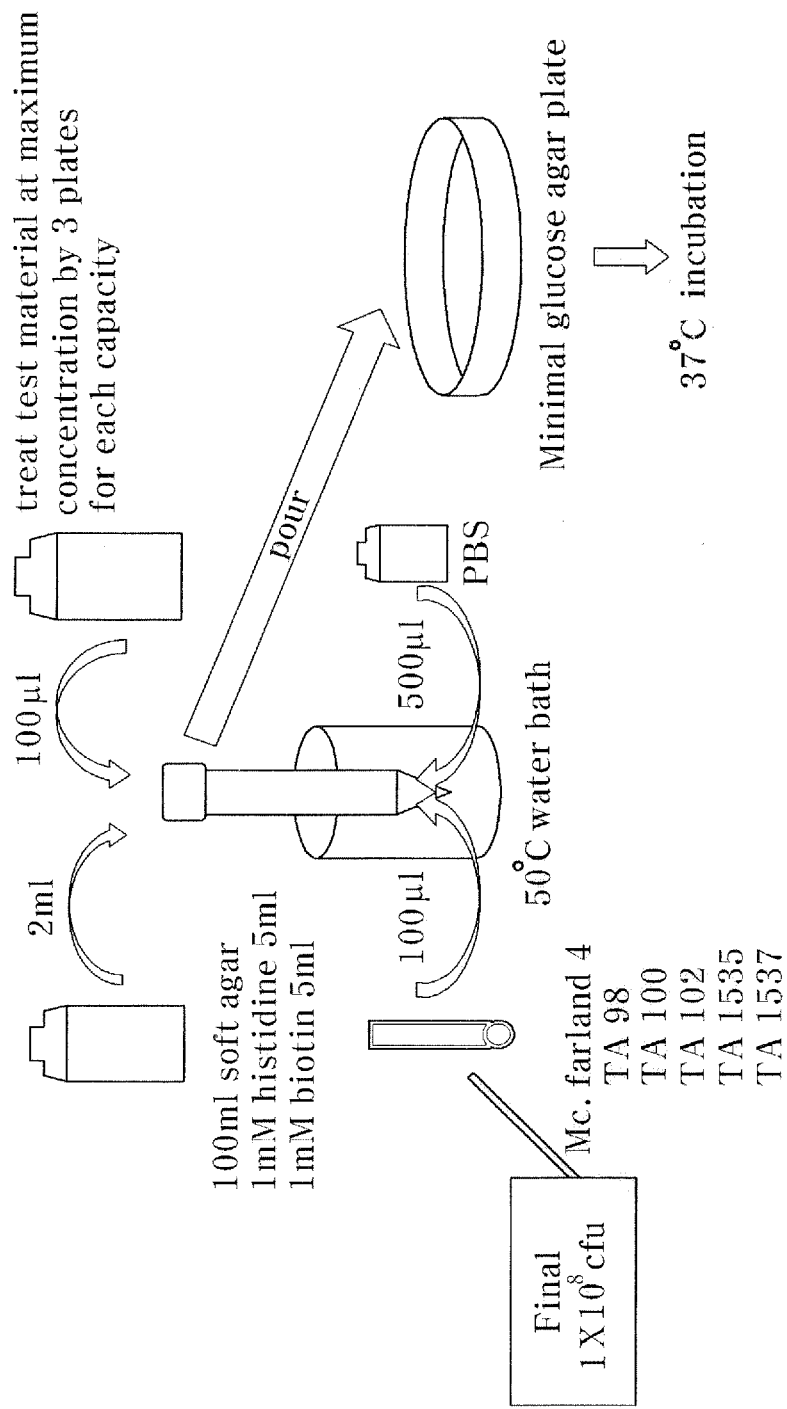
FIG. 1 illustrates a test procedure of a microorganism reverse mutation test.
Figure 2A:
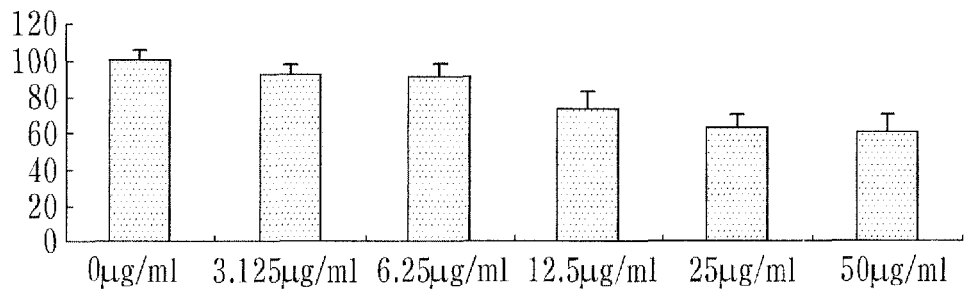
FIGS. 2A to 2D illustrate results of MTT assay on each cell after liver cancer cells (HepG2), lung cancer cells (NCI-H460), colon cancer cells (SW480), and breast cancer cells (MCF-7) are treated with a roasted chalcanthite (IS3), an egg white combined chalcanthite (IS4), and a raw chalcanthite (IS5), respectively.
Figure 2A:
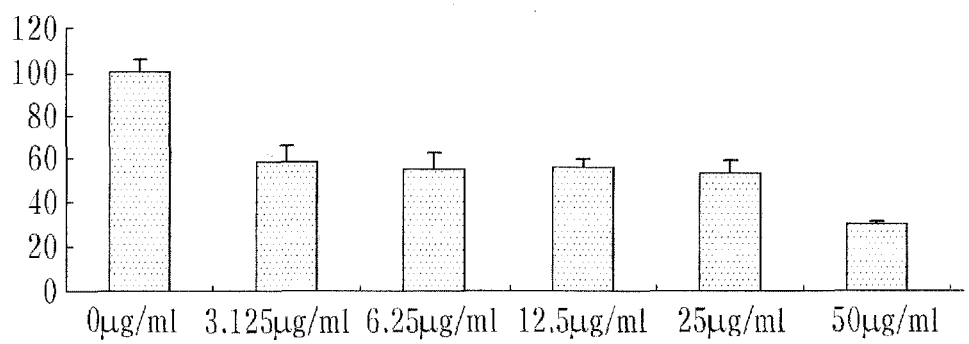
Figure 2A:
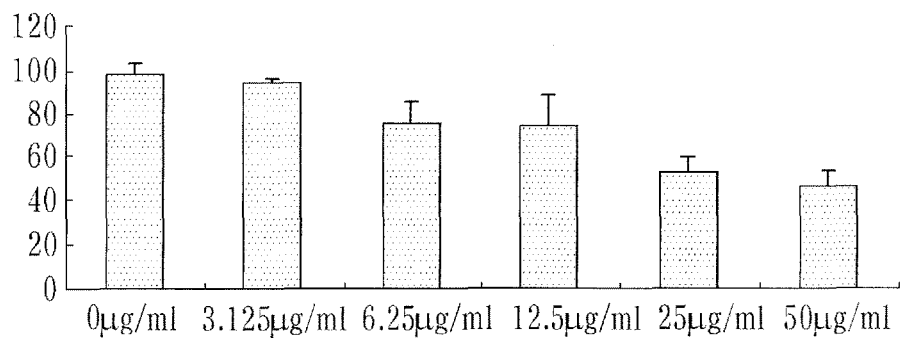
Figure 2B:
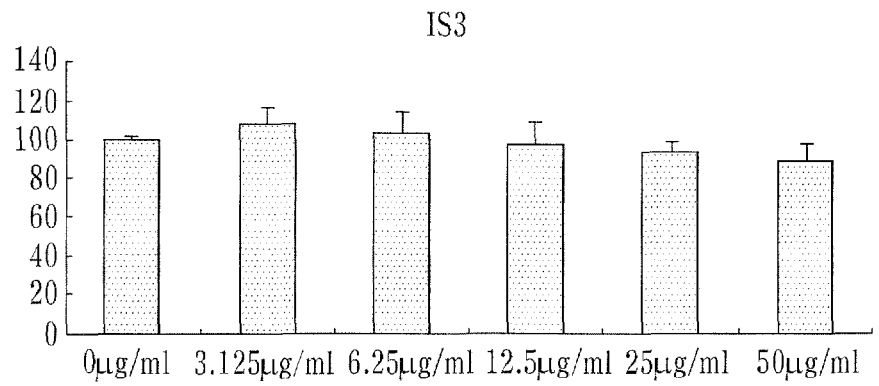
Figure 2B:
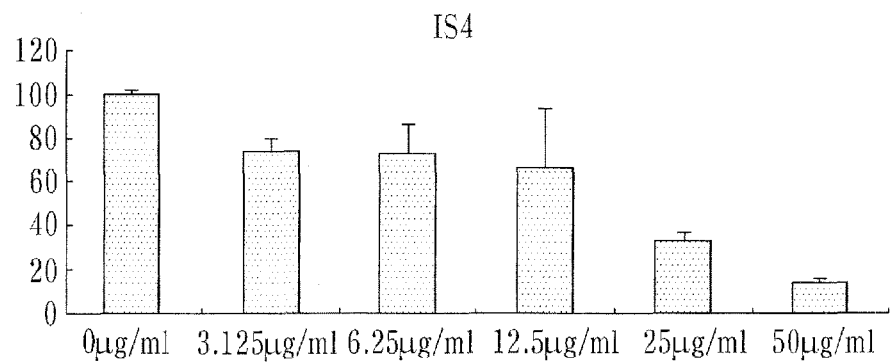
Figure 2B:
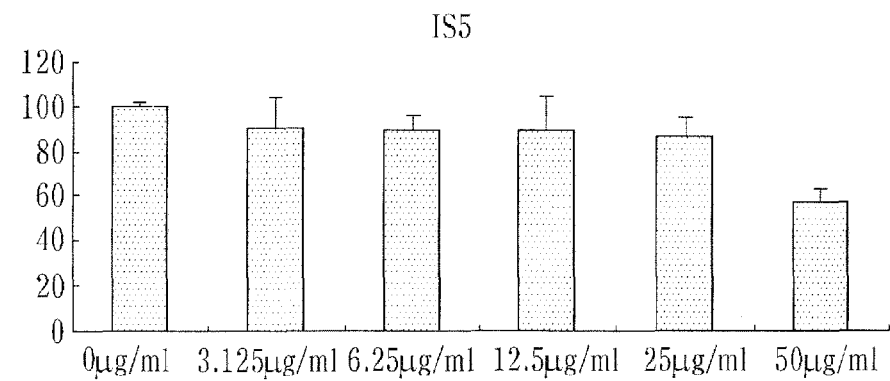
Figure 2C:
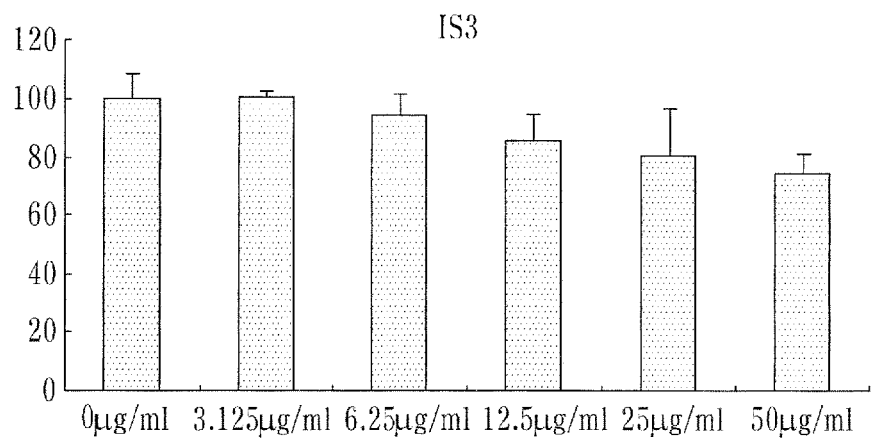
Figure 2C:
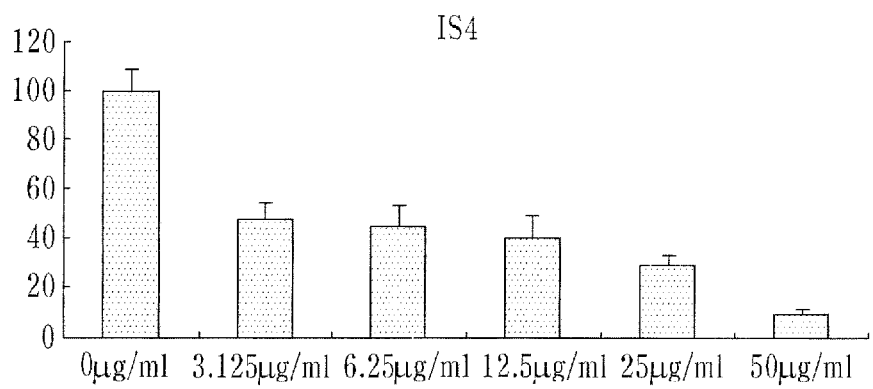
Figure 2C:
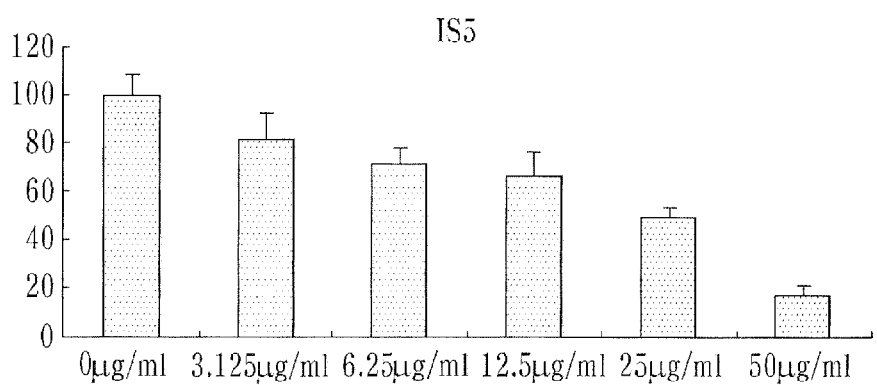
Figure 2D:
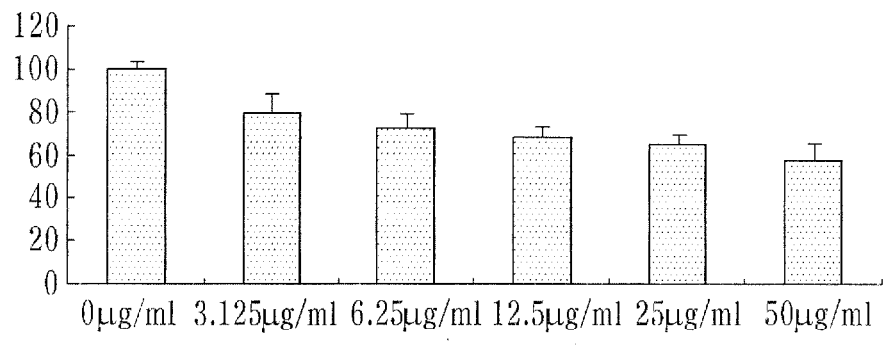
Figure 2D:
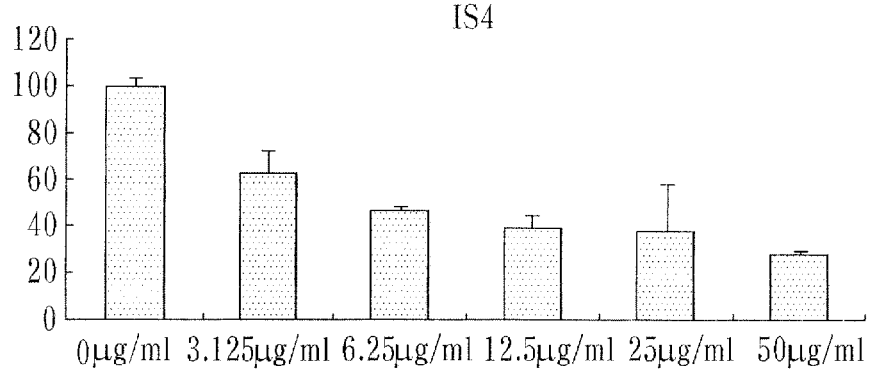
Figure 2D:
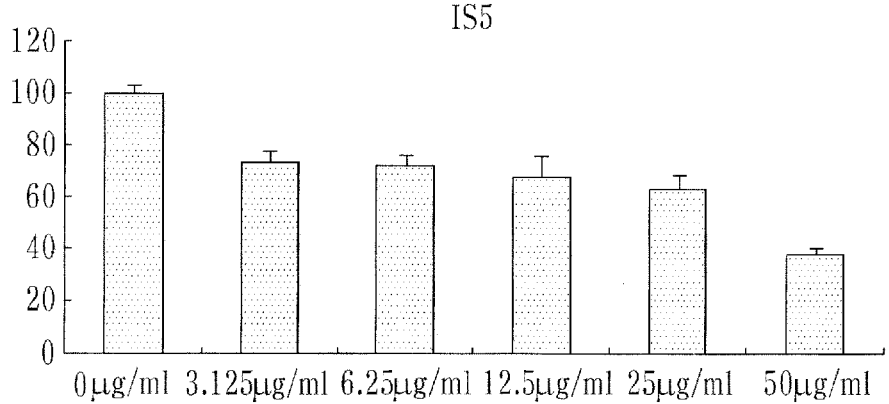

Hereinafter, a composition comprising egg white combined chalcanthite for preventing or treating cancer according to the present invention will be described in detail with reference to the accompanying drawings. However, below-described embodiments are merely provided for illustration of the present invention, not limiting to the present invention.

Example 1

Prepare Test Material (Raw Chalcanthite, Roasted Chalcanthite and Egg White Combined Chalcanthite)

A roasted chalcanthite obtained by roasting and dehydrating a raw chalcanthite and an egg white combined chalcanthite obtained by processing a roasted chalcanthite with egg white were prepared. In this test, the raw chalcanthite, the roasted chalcanthite and the egg white combined chalcanthite were utilized.

First, the roasted chalcanthite is prepared by heating and dehydrating the raw chalcanthite. To be specific, when the raw chalcanthite is roasted for 24 hours, the raw chalcanthite turns grey because it is dehydrated. Such a dehydrated chalcanthite is referred to as 'roasted chalcanthite'. After the roasted chalcanthite is completely cooled, it is finely pulverized.

The egg white combined chalcanthite is prepared by mixing and reacting the roasted chalcanthite powder with egg white. To be specific, 600 g of the roasted chalcanthite powder is mixed with 260 g of egg white that is separated from 13 homegrown eggs, and then reacts with moisture contained in the egg white to generate a great amount of heat (reaction heat). As a result, the chalcanthite turns green and the powders are agglomerated, which is referred to as 'egg white combined chalcanthite'.

To use the roasted chalcanthite (IS3), the egg white combined chalcanthite (IS4) and the raw chalcanthite (IS5) as test materials, respectively, each was weighed to 100 mg by a balance, and then dissolved in D.D.W to prepare a mixture with total volume of 1 ml. After the test materials were fully dissolved, a supernatant was filleted with 0.8-µm syringe filter by centrifuging the mixture at 600 rpm.

| | Test material | Total vol. | Particulars | Filter size | Remarks |
|---|---|---|---|---|---|
| Dissolved in D. W | IS3 Roasted chalcanthite | 100 mg/ml | Dissolved by 97%(about 30 μg precipitated) | 0.8 μm filter | After filtering, supernatant is used after being rotated at 6,000 rpm for 10 min. |
| | IS4 Egg white-chalcanthite | 100 mg/ml | Very small amount of white powder remains | 0.8 μm filter | |
| | IS5 Raw chalcanthite | 100 mg/ml | Dissolved | 0.8 μm filter | |

Example 2

Microorganism Reverse Mutation Test for Genetic Toxic Test

To measure genetic toxic degrees of the roasted chalcanthite and the egg white combined chalcanthite, a microorganism reverse mutation test that can detect a cell mutagen was performed.

The principle of this test is to make use of histidine-requiring strains that are not alive without histidine. This test is performed for detecting histidine recovery, which is original strain property, caused by mutagen in a mutant test. In the test, if the number of strains exceeds two times the number of untreated group (negative control group) or increases depending on the concentration of the test material, the test result is determined positive, and it is concluded as a mutagen.

To carry out the microorganism reverse mutation test, the test was conducted on test standard strains, *salmonella typimurium* TA98, TA100, TA1535 and TA1537 as pre-culture. A tolerance test was performed first, and thereafter two strains, i.e., *salmonella typimurium* TA100 and TA102, were selected as test strains among the strains exhibiting tolerance against the chalcanthite. The *salmonella typimurium* TA100 is a test strain upon the reversion of guanine and cytosine in a gene, and the *salmonella typimurium* TA102 is a test strain upon the reversion of adenine and thymine.

When an antibacterial test was performed on cells using the egg white combined chalcanthite (5,000 μg/plate) and the roasted chalcanthite (2,500 μg/plate), it was observed that the growth of the strains were suppressed. Therefore, the genetic toxic (reverse mutation) test was performed at below-described concentrations where the strain growth was not suppressed (see FIG. 1).

The egg white combined chalcanthite having the concentrations of 1,250, 625, 313, 156, and 78 μg/plate are used as a treated group while setting the maximum concentration to 2,500 μg/plate. Also, the roasted chalcanthite having the concentrations of 625, 313, 156, and 78 μg/plate are also used as the treated group while setting the maximum concentration to 1,250 μg/plate.

As a positive control group, sodium azide with the concentration of 1 μg/plate (for treating *salmonella typhimurium* TA100) and mitomycin C with the concentration of 1 μg/plate (*Salmonella typhimurium* TA102) were used. As a negative control group, distilled water was used.

The respective test materials, positive control group chemicals, distilled water were treated on a plate, and thereafter the number of revertant strains was measured. The results are as follows.

TABLE 1

| Egg white-chalcanthite, Strain: TA100 | | | | | | | | |
|---|---|---|---|---|---|---|---|---|
| Concentration (μg/plate) | Positive control | Negative control | Treated | | | | | |
| | 1 | 0 | 2,500 | 1,250 | 625 | 313 | 156 | 78 |
| Number | 1,136 | 194 | 241 | 195 | 157 | 142 | 159 | 186 |
| | 1,421 | 211 | 205 | 221 | 184 | 173 | 162 | 162 |
| Average | 1,279 | 202 | 223 | 208 | 171 | 158 | 161 | 174 |

| Roasted chalcanthite, Strain: TA100 | | | | | | | |
|---|---|---|---|---|---|---|---|
| Concentration (μg/plate) | Positive control | Negative control | Treated | | | | |
| | 1 | 0 | 1,250 | 625 | 313 | 156 | 78 |
| Number | 1,662 | 237 | 192 | 186 | 193 | 192 | 173 |
| | 1,456 | 201 | 235 | 179 | 182 | 193 | 169 |
| Average | 1,559 | 219 | 214 | 183 | 188 | 193 | 171 |

TABLE 2

| Egg white-chalcanthite, Strain: TA102 | | | | | | | | |
|---|---|---|---|---|---|---|---|---|
| Concentration (μg/plate) | Positive control | Negative control | Treated | | | | | |
| | 1 | 0 | 2,500 | 1,250 | 625 | 313 | 156 | 78 |
| Number | >1,000 | 5 | 3 | 4 | 2 | 1 | 0 | 2 |
| | >1,000 | 3 | 5 | 3 | 2 | 0 | 3 | 1 |

| Roasted chalcanthite, Strain: TA102 | | | | | | | |
|---|---|---|---|---|---|---|---|
| Concentration (μg/plate) | Positive control | Negative control | Treated | | | | |
| | 1 | 0 | 1,250 | 625 | 313 | 156 | 78 |
| Number | >1,000 | 2 | 2 | 4 | 1 | 3 | 0 |
| | >1,000 | 3 | 1 | 0 | 3 | 4 | 2 |

In the case of the *salmonella typimurium* TA100, the number of strains in the group treated with the egg white combined chalcanthite and roasted chalcanthite were remarkably smaller than that of the positive control group and even similar to that of the negative control group at the maximum concentration not inducing the growth suppression of microorganisms. Furthermore, the number of colonies was not increased depending on the concentration. Therefore, it was determined that the egg white combined chalcanthite and the roasted chalcanthite were not mutagens.

Also, in the case of the *salmonella typimurium* TA102, colonies rarely appeared in the group treated with the egg white combined chalcanthite and roasted chalcanthite at the maximum concentration not inducing the growth suppression of microorganisms. That is, the number of colonies in the group treated with the egg white combined chalcanthite and roasted chalcanthite was remarkably smaller than that of the positive control group, and even similar to that of the negative control group. In addition, the number of colonies was not increased depending on the concentration. Consequently, it was determined that the egg white combined chalcanthite and the roasted chalcanthite were not mutagens.

Example 3

Cancer Cell Culture

10% FBS, 100 U/ml penicillin and 100 U/ml streptomycin were put into RPM1640 medium (containing L-glutamine) and lung cancer cells (NCI-H460) were cultured in 5% $CO_2$ incubator.

Colon cancer cells (SW480) and breast cancer cells (MCF-7) were cultured under the same conditions as the lung cancers (NCI-H460).

10% FBS, 100 U/ml penicillin and 100 U/ml streptomycin were put into DMEM medium (containing L-glutamine) and liver cancer cells (HepG2) were cultured in 5% $CO_2$ culture medium.

The NCI-H460, MCF-7, SW480 and HepG2 cells were obtained from Korean Cell Line Bank (KLCB) and then used.

Example 4

Measurement of Cell Viability Through MTT (3-(4,5-Dimethylthiazol-2-yl) 2,5-Diphenyl Tetrazolium Bromide) Assay To investigate the effects of the roasted chalcanthite (IS3), egg white combined chalcanthite (IS4) and raw chalcanthite (IS5) on the growth of cancer cells, these materials were treated onto the cancer cells at various concentrations to measure cell viability, thereby assaying the suppression of the cancer cell growth.

The MTT assay was performed on four cancer cells, i.e., liver cancer cell (HepG2), colon cancer cell (SW480), breast cancer cell (MCF-7) and lung cancer cell (NCI-H460). First, each cell was inoculated into a 96-well plate at a concentration of $1\times10^5$ cells/ml by 100 µl, and the well plate was then cultured for 24 hours in 5% $CO_2$ incubator at 37° C. Thereafter, 100 µl of each test material (IS3, IS4 and IS5) was put into wells at the concentration of 0, 3.125, 6.25, 12.5, 25, and 50 µg/ml, respectively, and then treated for 24 hours.

MTT (thyazolyl blue, SIGMA Co.) with the concentration of 2 mg/ml was prepared, and added to the wells by 15 µl to react with the test materials for 3 to 4 hours. 115 µl of the test material was removed from each well to leave only 30 µl of a violet material, and then 150 µl of dimethyl sulfoxide (DMSO) is added. Afterwards, the resultant was sufficiently mixed for 10 minutes in a microplate mixer to dissolve precipitates, and then optical density (OD) was measured with the absorbance of 540 nm in a micro-reader. All the test results were compensated by the absorbance measured in the well in which cells were not cultured.

In all samples, the growth suppression effect appears as the concentration increases. Especially, it can be observed that the growth of cancer cells is most effectively suppressed when the cancer cells are treated with the egg white combined chalcanthite (IS4) (See FIGS. 2A to 2D)

Example 5

Cell Apoptosis Assay Using DAPI Staining

To observe how the roasted chalcanthite (IS3), egg white combined chalcanthite (IS4) and raw chalcanthite (IS5) suppress cell growth by inducing apoptosis of cancer cells (NCI-H460 and HepG2), the cancer cells were treated with each test material. Then, the cancer cells were stained with DAPI, and cell types were observed through a fluorescence microscope. Specific test procedure is as follows.

400 µl of each cell ($1\times10^5$ cell/ml) was put in a 8-well chamber slide and cultured for 24 hours. Thereafter, the cultured cells were treated with the test material having the concentration of 50 µg/ml and made to react for 24 hours. After the reaction, the medium is discarded and the cells react with 500 µl of 75 mM KCL. This expands the cells to make it easy to observe nucleus. After making cold-ice state by mixing acetic acid and methanol at a ratio of 1:3, this was dispensed in a volume of 500 µl to react for 5 minutes, thereby immobilizing the cells. This procedure was repeated twice. After immobilized, the resultant is sufficiently dried in air, and 100 µl of DAPI stain solution was dropped to stain the resultant for 10 minutes, and thereafter washed with PBS. A cover glass was covered with glycerol and the resultant cells were observed through a fluorescence microscope ($\times100$, or $\times200$). Among three hundred cells counted, the cells exhibiting nuclear fragmentation and chromatin condensation were detected and observed according to the morphologic criteria of apoptosis.

It has been reported that apoptosis, which is programmed cell death, accompanies cell shrinkage, chromatin condensation, DNA fragmentation, mitochondria dysfunction, caspase protease activation. DAPI is a blue fluorescent stain, and has characteristic that fluorescence increases when it bonds with minor grooves in which AT clusters of DNA exist. In virtue of this characteristic, it is possible to visibly observe the degree of DNA fragmentation by simply checking fragmented and condensed apoptotic bodies through a microscope.

Figure 3A:
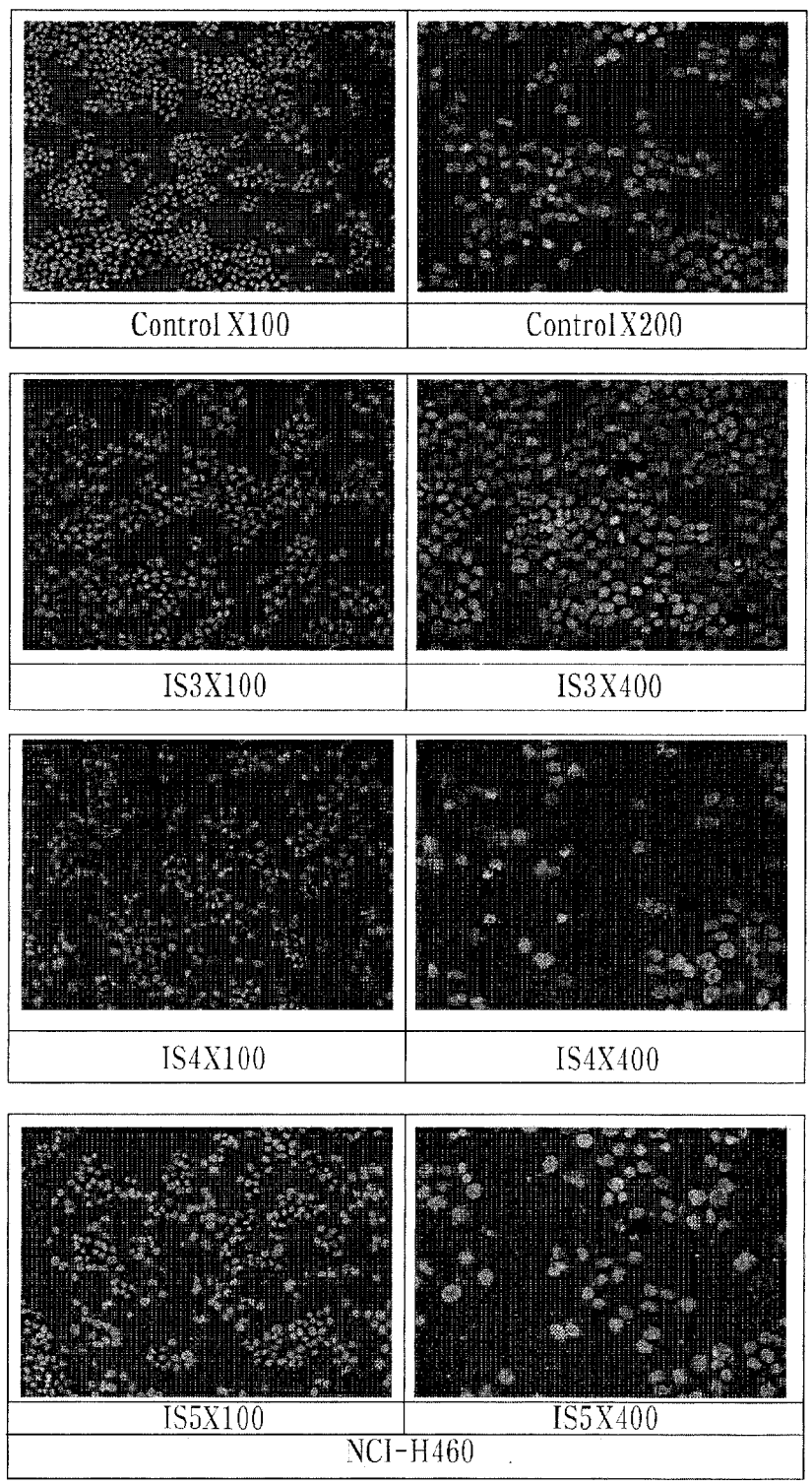
FIGS. 3A and 3B illustrate results of DAPI stained cells after NC-H460 and HepG2 cells are treated with a roasted chalcanthite (IS3) and an egg white combined chalcanthite (IS4) having concentrations of 50 µg/ml, respectively.
Figure 3B:
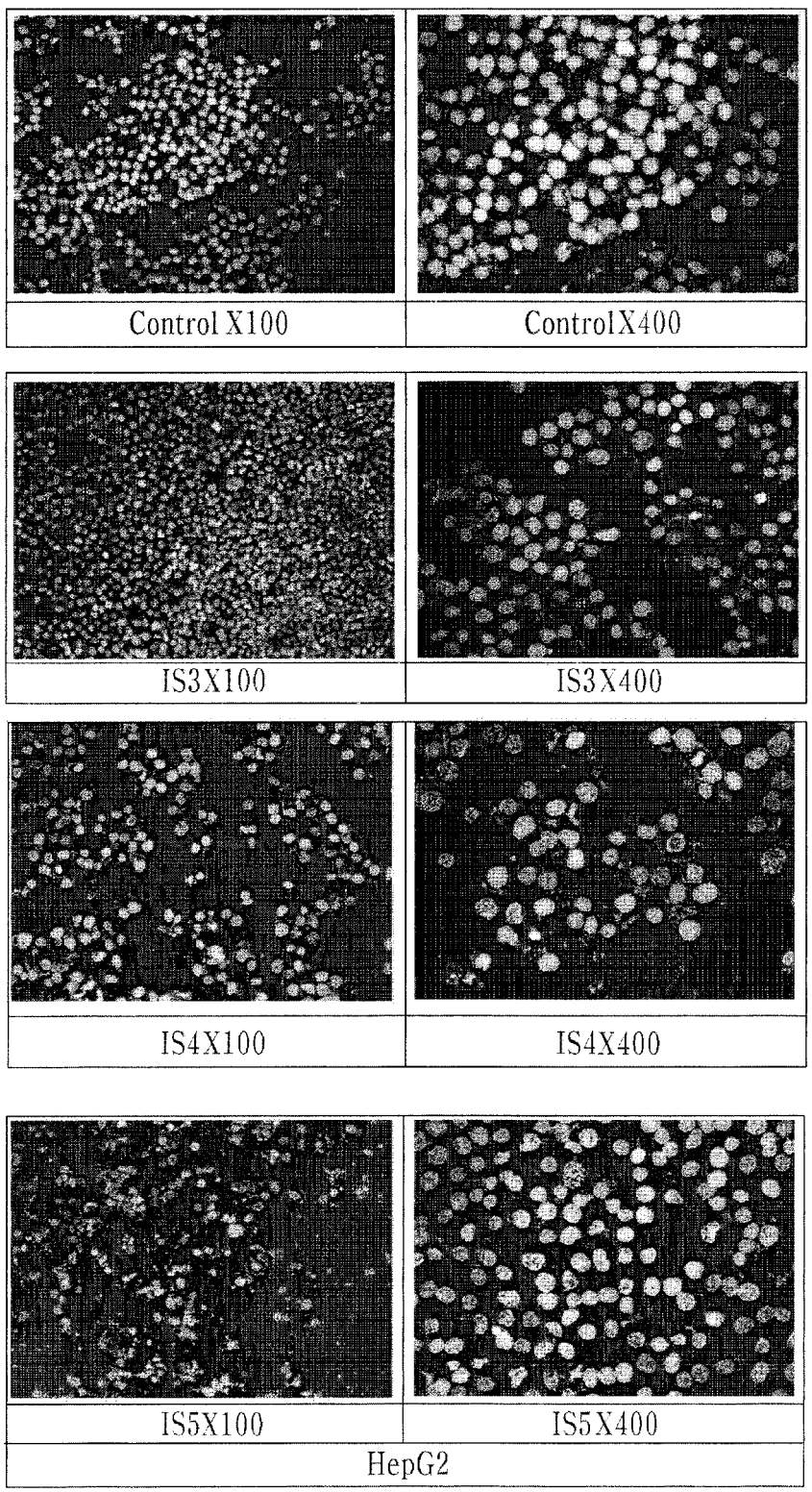

DAPI staining was performed on H460 and HepG2 cells, which had been treated with the roasted chalcanthite (13) and the egg white combined chalcanthite (14) having at the concentration of 50 µg/ml. In comparison with the control group (group untreated with the chalcanthite), nuclear fragmentation and chromatin condensation could be observed in all the cells. Particularly, it was possible to observe many apoptotic bodies in the egg white combined chalcanthite (IS4) (See FIGS. 3A and 3B).

Example 6

Detection of Apoptosis-Related Protein Expression by Western Blot Test

The control degree of expression of apoptosis-related protein, e.g., caspase-3, bax and bcl-2 was observed in order to observe the effect of the egg white combined chalcanthite upon cancer cells at a protein level.

Bax functions to induce apoptosis by promoting the secretion of cytochrome C while moving from cytosol to mitochondria. In contrast, it is known that bcl-2 acts as an important signal transferring system that transfers or receives situations in or outside cells, and inhibits the movement of bax to mitochondria to thereby suppress apoptosis (Nomura et al., 1999; Murphy et al., 2000).

Caspase-3 is most directly associated with apoptosis, and acts at an initial stage of apoptosis. Further, caspase-3 has an active form of heterodimer of 17 kDa and 19 kDa derived by the separation of 35 kDa proenzyme (Fernandes-Alnemri et al., 1994), and amplifies initial signals of caspase-8 and caspase-9.

The apoptosis is classified into an internal path and an external path, which induce apoptosis through caspase-3 activity. In order for caspase-3 to be observed in an active form, the expression degree of procaspase-3 of inactive 35 kDa should be reduced relatively or a protein having a molecular weight of 17 kDa and 19 kDa which is an active form thereof should be detected (Kang et al., 2002; Ahn et al., 2004).

A western blot test was performed to observe whether the egg white combined chalcanthite (IS4) controls the expression of proteins (e.g., caspase-3, bax and bcl-2) that has been known to induce apoptosis. Through this test, it was possible to know a path through which the egg white combined chalcanthite induces apoptosis in cells. Specific test procedure is as follows.

Lung cancer cells (NCI-H460) were treated with the egg white combined chalcanthite (IS4) at concentrations of 0, 25, 50 and 100 µg/ml, respectively, and then cultured for 24 hours at 37° C. Thereafter, the cells are collected using a scrapper, the collected cells were centrifuged at 1,000 rpm together with a medium containing them, a supernatant was removed, and then washed twice with 2 ml cold PBS. 50 to 100 µl of lysis buffer is added to the resultant and sufficiently mixed, and then dissolved for 2 hours at 4° C. Herein, the lysis buffer is composed of 50 mM Tris pH 8.0, 150 mM NaCl, 0.02% sodium azide, 0.2% SDS, 100 µg/ml of PMSF (phenylmethylsulfonnyl fluoride), 50 µl/ml of aprotinin, 1% igapel 630 (or NP-40), 100 mM NaF, 0.5% sodium deoxycholate, 0.5 mM EDTA (Ethylnediamineetraacetic acid—Sigma E-4884), and 0.1 mM EGTA (Ethylene glycol-bis(β-aminoethylether) N,N,N',N'-tetraacetic acid—sigma E-4378). After the reaction, the test material is put into a 1.5-ml tube, then stirred for 30 seconds, and centrifuged for 1 hour at 23,000 g at 4° C. Only centrifuged supernatant was taken. The protein amount of a final test material was measured using a bio-rad protein kit. Lysis buffer and 5× sample buffer are mixed with the measured protein to make the protein amount equal, and then the resultant was boiled for 5 minutes in a 100° C. heat block. After that, a test material is collected by centrifuging the resultant for a while. After preparing a separating gel (12.5%) and a stacking gel (5%), an electrophresis is performed and the gel is then transferred. Transferred gel was dipped in a staining solution (Coomassie blue staining solution) for 10 minutes, and brought into a destaining solution to observe remaining proteins. A transferred membrane was washed with TBS-T solution and a bit of moisture was then removed. Thereafter, the membrane is blocked for 2 hours with about 5% skim milk diluted with TBS-T solution, and washed several times with TBS-T solution. After reacting with a primary antibody (bax, bcl-2, cleaved caspase-3; cellsignaling) and secondary antibody (anti-rabbit) followed by the reaction in ECL solution for 1 minute, a film was placed on a cassette, and was observed through photographing and developing.

Figure 4:
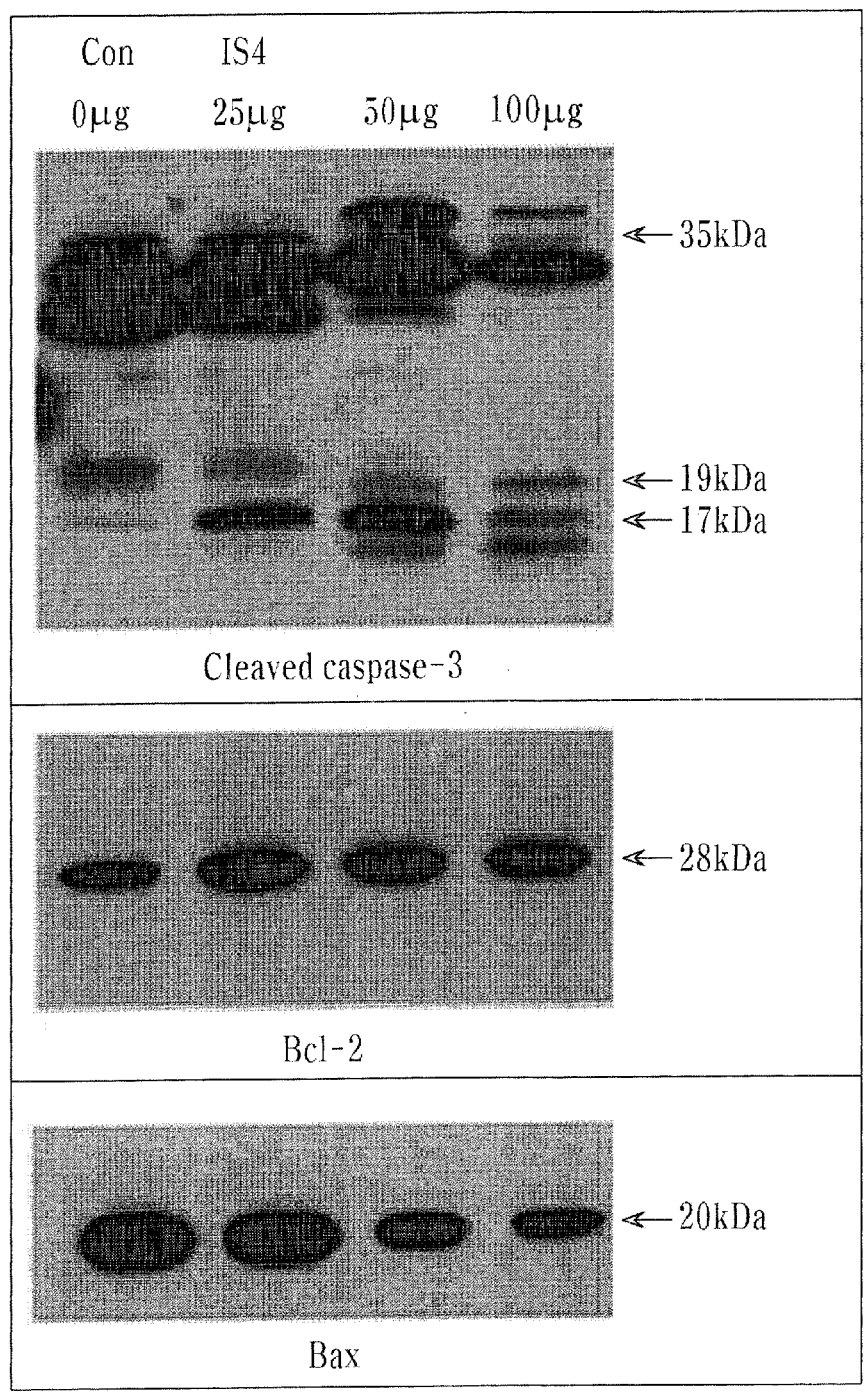
FIG. 4 illustrates results of a western blot test to observe the protein expression degree of cells after NCI-H460 cells are treated with an egg white combined chalcanthite (IS4) having various concentrations.

As a result of the treatment of H460 cells with the egg white combined chalcanthite (IS4), the expression of cleaved caspase-3 tends to increase at 25 µg/ml and 50 µg/ml, but tends to slightly decrease at 100 µg/ml. It is considered that this is because the test material with higher concentrations exhibit toxicity. The expression of bcl-2 slightly increases but the expression of bax decreases in the group treated with the egg white combined chalcanthite (IS4) (see FIG. 4).

From these results, it can be confirmed that the egg white combined chalcanthite, which is a mainly effective component of the inventive composition, activates caspase-3 protein in cancer cells to thereby induce apoptosis. Also, it can be appreciated that the apoptosis is induced by activating caspase-3 protein through a path differing from a bax/bcl-2 path.

Example 7

Treatment Cases

An egg white combined chalcanthite bamboo salt was prepared by mixing egg white combined chalcanthite and bamboo salt powder at a weight ratio of 1:20, and thereafter a powder mixture of the egg white combined chalcanthite and the bamboo salt was put into a capsule and then provided to patients. 10 to 20 capsules were administered per one day by swallowing the capsules one by one with saliva or drinking water (one-day administration dose is 5 to 10 g in total on the basis of an adult, or 1 to 3 capsules per 10 kg in body weight). The patients took the capsules over 2 to 10 times at intervals of 1 to 2 hours. If necessary, herbal decoction and Sari-Jang for recovering energy was administered together with the egg white combined chalcanthite bamboo salt.

<7-1> Case 1. Treatment of Breast Cancer

Patient information (surname: Won, age: 44, gender: female): She was diagnosed with stage II breast cancer but did not receive neither operation nor chemical therapy. Instead, she took herbal decoction, egg white combined chalcanthite bamboo salt, and Sari-Jang, and resultantly was perfectly cured after 5 months.

<7-2> Case 2. Treatment of Leukemia

Patient information (surname: Cho, age: 8, gender: male): He gave up tertiary chemical therapy and bone-marrow transplant after the secondary chemical therapy, but took herbal decoction, egg white combined chalcanthite bamboo salt, and Sari-Jang for 3 months. Thereafter, a blood test was carried out, and test results (ANC1760-erythrocyte14.3-thrombocyte202K) demonstrated that all blood parameters are in normal ranges.

<7-3> Case 3. Treatment of Stomach Cancer

Patient information (surname: Kang, age: 55, gender: male): He took herbal decoction, egg white combined chalcanthite bamboo salt, and Sari-Jang for 3 months in a state of stage III stomach cancer with liver cancer metastasis (six tumors with 8 mm in size). Thereafter, CT test was carried out, and the test result proved that the stomach and liver cancer cells shrunk in size (two of the six tumors disappeared and the remaining four shrunk in size by half). Furthermore, another CT test after the additional 2-month administration demonstrated that three tumors disappeared, two tumors were blurred, one tumor shrunk in size by half, and only one of the six tumors remained.

<7-4> Case 4. Treatment of Dysplasia of Cervix Uteri

Patient information (surname: Ko, age: 35, gender: female): She was afflicted with dysplasia of cervix uteri, has taken antituberculosis drugs for 2 years, and had hepatitis B virus carriers. In this state, she took herbal decoction, egg white combined chalcanthite bamboo salt, and Sari-Jang for 3 months, and further egg white combined chalcanthite bamboo salt water was injected into the uterus. After that, an inspection was carried out, and she was diagnosed that most of cells became normal and only nucleus was slightly enlarged. Thereafter, she relapsed into the disease due to the interruption of administration. However, she was re-treated (that is, took the herbal decoction and egg white combined chalcanthite bamboo salt, and the egg white combined chalcanthite bamboo salt is injected), and resultantly was perfectly cured after 1 month.

<7-5> Case 5. Treatment of Colon Cancer, Lung Cancer, and Bone Cancer

Patient information (surname: Chun, age: 57, gender: male): He was diagnosed with colon cancer, lung cancer, and bone cancer (cervical vertebrae cancer). After he had received operations for excising colon cancer and lung cancer (when an inspection had been carried out due to urination problem at that time, a bladder is normal but a portion of a bladder had been excised because it had pressed down the nerve), the cancer metastasized to the vertebrae. The vertebrae was then destructed by the growth of cancer cells, and thus nerves around a rib are pressed down so that he suffered from severe pain. In spite of 6-times chemical therapy, his conditions was not improved at all but the cancer cells remained intact. There was no therapeutic possibility, and he could not help withstanding the pain with an anodyne everyday because he was too weak to receive chemical therapy. However, in this situation, herbal decoction, egg white combined chalcanthite bamboo salt, and Sari-Jang were administered to him for 5 months. After that, he underwent a medical examination, and the examination result proved that he was perfectly cured.

<7-6> Case 6. Treatment of Thyroid Cancer

Patient information (surname: Kim, age: 46, gender: male): He was treated for acute hepatitis 12 years ago, and currently his liver is calcified. After being diagnosed with thyroid cancer, he took herbal decoction, egg white combined chalcanthite bamboo salt, and Sari-Jang without chemical therapy. One month later, CT inspection result demonstrated that the size of the cancer was reduced to 4.6 mm from 5.1 mm. After additional administration for 6 months, he was perfectly cured.

According to the present invention, since the toxicity of the chalcanthite is removed but the pharmaceutical activity of the chalcanthite is maximized in the composition comprising the egg white combined chalcanthite, the composition comprising the egg white combined chalcanthite exhibits excellent anti-cancer activity. Consequently, the composition of the present invention can be usefully applied to pharmaceutical preparations for preventing or treating cancer, and also be applicable to heath functional foods.

While the present invention has been described with respect to the specific embodiments, it will be apparent to those skilled in the art that various changes and modifications may be made without departing from the spirit and scope of the invention as defined in the following claims.

What is claimed is:

1. A pharmaceutical composition for treating cancer, comprising a ratio of egg white to chalcanthite effective for treating cancer, wherein the egg white is combined with chalcanthite powder prepared by a process comprising roasting chalcanthite, pulverizing the roasted chalcanthite, mixing the pulverized chalcanthite with egg white and then reacting the moisture contained in the egg white to generate a reaction heat.

2. The composition of claim 1, further comprising a bamboo salt.

3. The composition of claim 2, wherein the egg white combined with chalcanthite and the bamboo salt powder are mixed at a ratio of approximately 1:5 to approximately 1:50 by weight.

4. The composition of claim 1, further comprising a pharmaceutically acceptable carrier.

5. The composition of claim 2, further comprising a pharmaceutically acceptable carrier.

6. A method for preparing egg white-chalcanthite, wherein the ratio of the egg white to chalcanthite is effective for treating cancer, the method comprising: heating and dehydrating a chalcanthite, until the entire chalcanthite turns grey; cooling the dehydrated chalcanthite; pulverizing the chalcanthite; mixing the chalcanthite with egg white at the effective ratio; and then reacting the moisture contained in the egg white to generate a reaction heat.

7. The method of claim 6, further comprising, after mixing the chalcanthite with egg white, cooling the egg white-chalcanthite mixture, and pulverizing the mixture.

8. The method of claim 6, wherein the ratio of chalcanthite to egg white is the same proportion as when 600 g of the dehydrated chalcanthite powder is mixed with from 140 g to 400 g of egg white.

9. A method of increasing caspase-3 activity in a subject comprising administering an effective amount of the composition of claim 1 to the subject.

10. A method of inhibiting growth of cancer cells comprising administering to the cells an effective amount of the composition of claim 1.

11. The method of claim 10, wherein the cancer cells are a type selected from the group consisting of liver cancer, breast cancer, lung cancer, colon cancer, stomach cancer, pancreatic cancer, uterine cancer, prostate cancer, bone cancer, glioma, and leukemia.

12. A method of increasing caspase-3 activity in a subject comprising administering an effective amount of the composition of claim 2 to the subject.

13. A method of inhibiting growth of cancer cells comprising administering to the cells an effective amount of the composition of claim 2.

14. The method of claim 13, wherein the cancer cells are a type selected from the group consisting of liver cancer, breast cancer, lung cancer, colon cancer, stomach cancer, pancreatic cancer, uterine cancer, prostate cancer, bone cancer, glioma, and leukemia.

15. The pharmaceutical composition of claim 1 wherein the pulverized chalcanthite and the egg white are mixed at a ratio of 600 g:140~400 g.

16. The pharmaceutical composition of claim 2 wherein the pulverized chalcanthite and the egg white are mixed at a ratio of 600 g:140~400 g.

17. The pharmaceutical composition of claim 3 wherein the egg white combined chalcanthite and the bamboo salt powder are mixed at a ratio of 1:5 to 1:30 by weight.

* * * * *